(12) United States Patent
Tucker et al.

(10) Patent No.: US 11,045,131 B1
(45) Date of Patent: Jun. 29, 2021

(54) TRUNCATED ICOSAHEDRAL NEURAL SENSOR NET AND MODULAR ELEMENTS THEREFOR

(71) Applicant: Brain Electrophysiology Laboratory Company, LLC, Eugene, OR (US)

(72) Inventors: Don M. Tucker, Eugene, OR (US); Phan Luu, Eugene, OR (US); Roman Shusterman, Eugene, OR (US)

(*) Notice: Subject to any disclaimer, the term of this patent is extended or adjusted under 35 U.S.C. 154(b) by 0 days.

(21) Appl. No.: 16/891,419

(22) Filed: Jun. 3, 2020

(51) Int. Cl.
*A61B 5/291* (2021.01)
*A61B 5/00* (2006.01)

(52) U.S. Cl.
CPC ............ *A61B 5/291* (2021.01); *A61B 5/6814* (2013.01); *A61B 2560/0412* (2013.01); *A61B 2560/0443* (2013.01)

(58) Field of Classification Search
CPC ... A61B 5/6814; A61B 5/6868; A61B 5/4064; A61B 5/04842; A61B 5/05; A61B 5/0496; A61B 5/0492; A61B 5/0488; A61B 5/0484; A61B 5/048; A61B 5/0482; A61B 5/0478; A61B 5/0476; A61B 5/291; A61B 2560/0468; A61B 2560/0462; A61B 2560/0443; A61B 2560/0406; A61B 2560/0412; A61B 2576/026; A61B 8/0808
See application file for complete search history.

(56) References Cited

U.S. PATENT DOCUMENTS

| | | | |
|---|---|---|---|
| 5,291,888 A | 3/1994 | Tucker | |
| 2009/0099473 A1* | 4/2009 | Dunseath | A61B 5/6814 600/544 |
| 2010/0274153 A1* | 10/2010 | Tucker | A61B 5/6814 600/544 |
| 2017/0281086 A1* | 10/2017 | Donaldson | A61B 5/14532 |
| 2018/0117352 A1* | 5/2018 | Rastogi | A61B 5/245 |
| 2018/0153722 A1* | 6/2018 | Cromie | A61B 5/6811 |
| 2020/0022581 A1* | 1/2020 | Vanegas | A61B 5/0064 |

* cited by examiner

*Primary Examiner* — Matthew Kremer
*Assistant Examiner* — Avery M Foley
(74) *Attorney, Agent, or Firm* — Birdwell & Janke, LLP

(57) ABSTRACT

A truncated icosahedral neural sensor net and modular elements therefor. The neural sensor net comprises a plurality of substantially pentagonally shaped elements connected to each other with elongate elastic tension lines at their respective vertices, the tension lines defining therebetween a plurality of substantially hexagonally shaped elements. The neural sensor net may be assembled from a plurality of modular elements.

16 Claims, 7 Drawing Sheets

TRUNCATED ICOSAHEDRAL NEURAL SENSOR NET AND MODULAR ELEMENTS THEREFOR

FIELD OF INVENTION

The present invention relates to wearable devices known in the art of neuroscience as "sensor nets" that are used to position electrodes on the surface of the head, which may be used for either or both brain measurement, such as electro-encephalography, and brain stimulation, such as transcranial electrical stimulation.

BACKGROUND

The present inventor originated the Geodesic Sensor Net ("GSN"), the subject of U.S. Pat. No. 5,291,888. The term "sensor" is used generically to refer to electrodes that can be used either for sensing or stimulation.

The GSN was modeled after an icosohedron or dodecohedron, and "tessellated" the head surface with sensors connected to each other by tension lines defining triangular shaped open spaces between the sensors in a substantially regular pattern.

The GSN was a highly successful concept, which has not been improved upon in the many years since the '888 patent issued.

The present invention is, however, such an improvement, that provides for a better fit to the head, and can also enable a reduction in manufacturing costs.

SUMMARY

Disclosed is a truncated icosahedral neural sensor net and modular elements therefor.

According to one aspect of the invention, a neural sensor net is provided that comprises a plurality of substantially pentagonally shaped elements connected to each other with elongate elastic tension lines at their respective vertices, the tension lines defining therebetween a plurality of substantially hexagonally shaped elements.

According to another aspect of the invention, a neural sensor net is assembled from a plurality of modular elements.

According to still another aspect of the invention, a modular element for a neural sensor net is provided, that comprises a body formed of a sheet material that defines a plurality of nodes and a plurality of tension lines, wherein the tension lines are elongate segments of the material that join the nodes so as to define the legs of triangles of which the nodes define vertices, wherein there are more than fifteen nodes and wherein, with the modular element laid flat, five of the more than fifteen nodes are connecting nodes that define the vertices of a pentagon, for connecting the modular element to one or more other modular elements, and ten of the more than fifteen nodes are closely spaced pairs of warping nodes disposed substantially mid-way between the vertices, wherein the nodes of each pair of warping nodes are separated by respective slits in the body of the modular element, the warping nodes and slits for warping the element into a 3D domed configuration for fitting to the head surface.

Optionally, the nodes may be annular in configuration.

Optionally, there may be at least one additional node that is a bridging node, adjacent and corresponding to one of the connecting nodes, to provide for sharing a tension line between the modular element and one other modular element.

Optionally, there may be five of the bridging nodes.

Optionally, the modular element may comprise an inner pentagonal element surrounded by an outer hexagonally tessellating structure.

Optionally, at least three substantially identical modular elements comprising respective inner pentagonal elements and outer hexagonally tessellating structure may be joined together so that the outer hexagonally tessellating structure of the three modular elements defines a hexagonal element between the three inner pentagonal elements of the three modular elements.

According to yet another aspect of the invention, an electrode assembly is provided for a neural sensor net that comprises a cap, a housing, and an electrode, the housing and cap adapted for snap fitting together so as to capture the electrode therebetween.

Optionally, the neural sensor net may be formed of a sheet material that defines a plurality of nodes and a plurality of tension lines, wherein the tension lines are elongate segments of the material that join the nodes so as to define the legs of triangles of which the nodes define vertices, and the housing and cap may be adapted for snap fitting together so as to capture one or more of the nodes therebetween.

Optionally, the electrode assembly may be configured for retaining an absorbent material that makes electrical contact with the electrode.

According to a further aspect of the invention, a process is provided for forming a neural sensor net, comprising forming a plurality of substantially identical, flat modules and connecting the modules together so as to warp the modules into a 3D domed configuration.

Preferably, the modules are substantially pentagonal in shape.

It is to be understood that this summary is provided as a means of generally determining what follows in the drawings and detailed description and is not intended to limit the scope of the invention. Objects, features and advantages of the invention will be readily understood upon consideration of the following detailed description taken in conjunction with the accompanying drawings.

DESCRIPTION OF PREFERRED EMBODIMENTS

The present invention provides for a truncated icosahedral neural sensor net, and it also provides for modular elements that may be used in combination with other modular elements to form a neural sensor net. The head is typically but not necessarily a human head, and the electrodes may be used for measuring electrical activity in the brain and/or for stimulating such activity.

Figure 1:
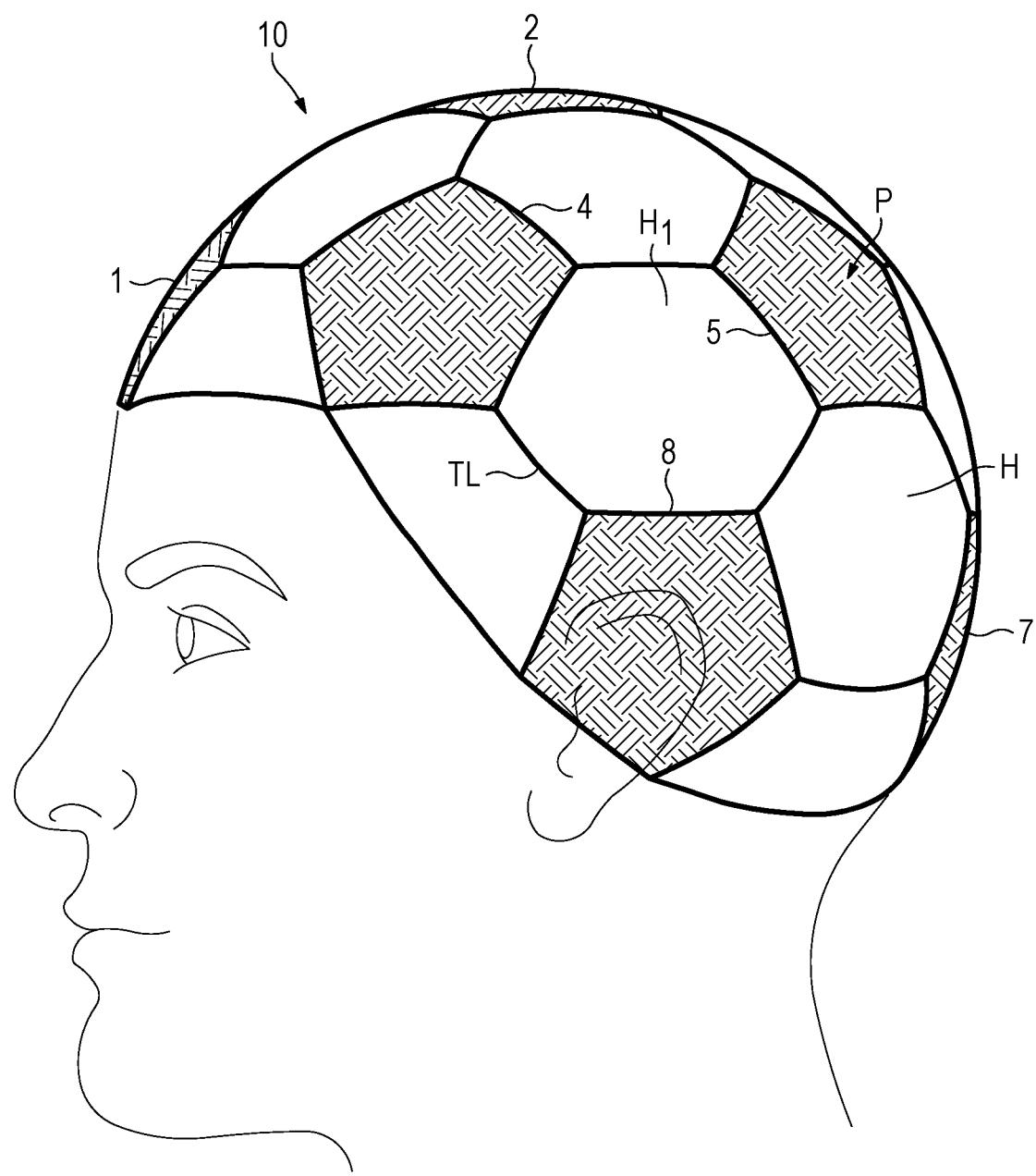
FIG. 1 is a schematic illustration of a truncated icosahedral neural sensor net according to the present invention.

FIG. 1 shows in schematic form a truncated icosahedral neural sensor net 10 according to the present invention. A regular icosahedron has twenty triangular faces; whereas a truncated icosahedron has thirty-two faces, twelve of which are pentagonal and twenty of which are hexagonal. As FIG. 1 shows, the truncated icosahedral neural sensor net 10 need only partially cover the head, and therefore does not need as many faces as the Archimedean solid.

Visible in FIG. 1 are five pentagonal elements "P," specifically referenced as 1, 2, 4, 5, 7, and 8, of the neural sensor net 10. The pentagonal elements P are connected to each other at their vertices by elastically extensible tension lines "TL." The tension lines, TL may be of any type that is known in the art of neural sensor nets. The tension lines TL define the perimeters of hexagonal elements "H" corresponding to hexagonal faces of a truncated icosahedron.

Figure 2:
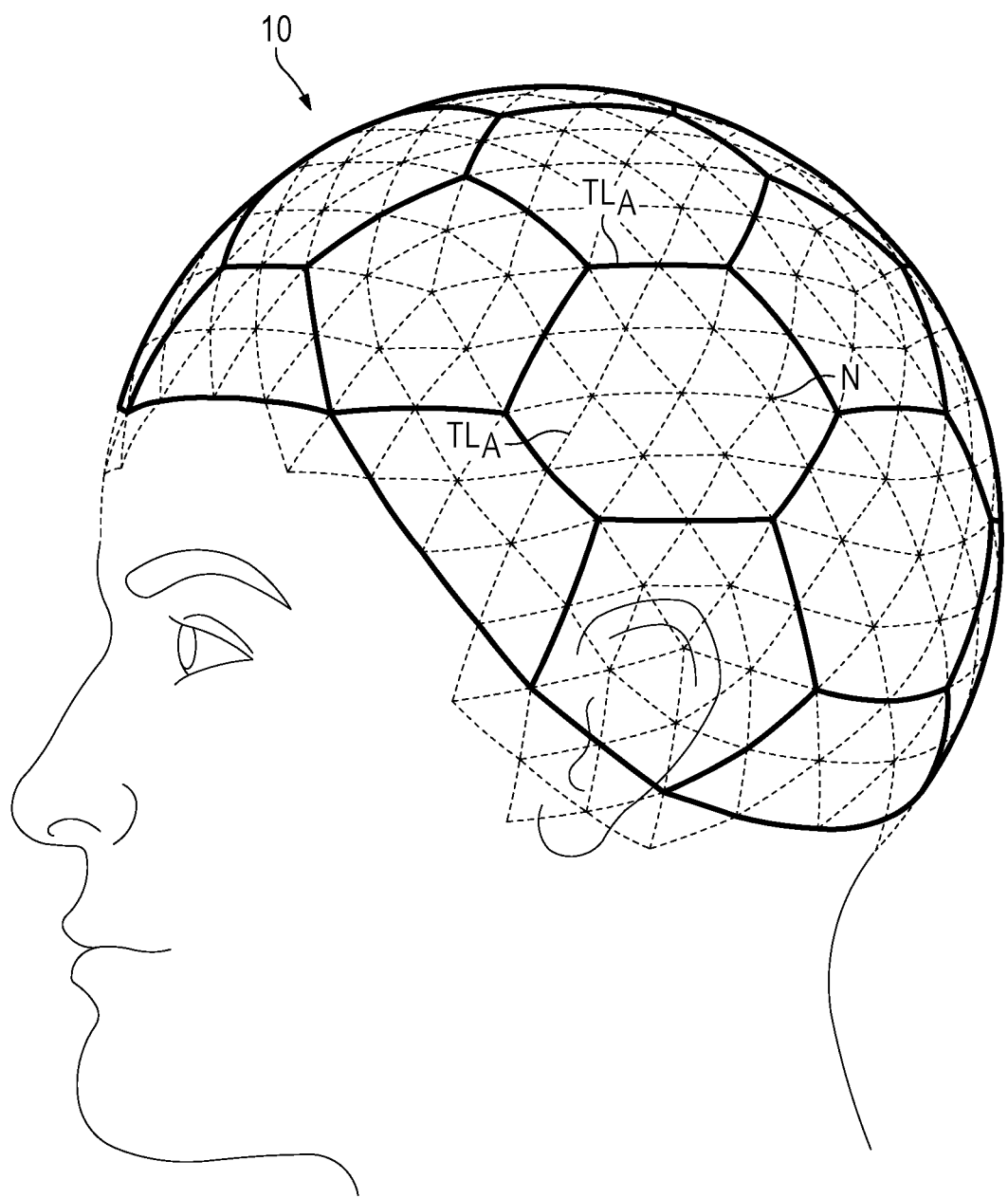
FIG. 2 is a less schematic illustration of the truncated icosahedral neural sensor net of FIG. 1.

FIG. 2 shows a more detailed representation of the sensor net 10 shown in FIG. 1. FIG. 2 shows how the interior portions of the elements P and E may be tessellated with more granular tension lines "$TL_A$," the intersections of which define nodes "N." The electrodes of the sensor net (not shown) would be located at the nodes N, respectively. At the level of generality of FIG. 1, the tessellation scheme is an equal mix of pentagonal and hexagonal; whereas in the preferred embodiment of FIG. 2 the tessellation scheme is hexagonal except at the centers of the pentagonal elements P.

Figure 3:
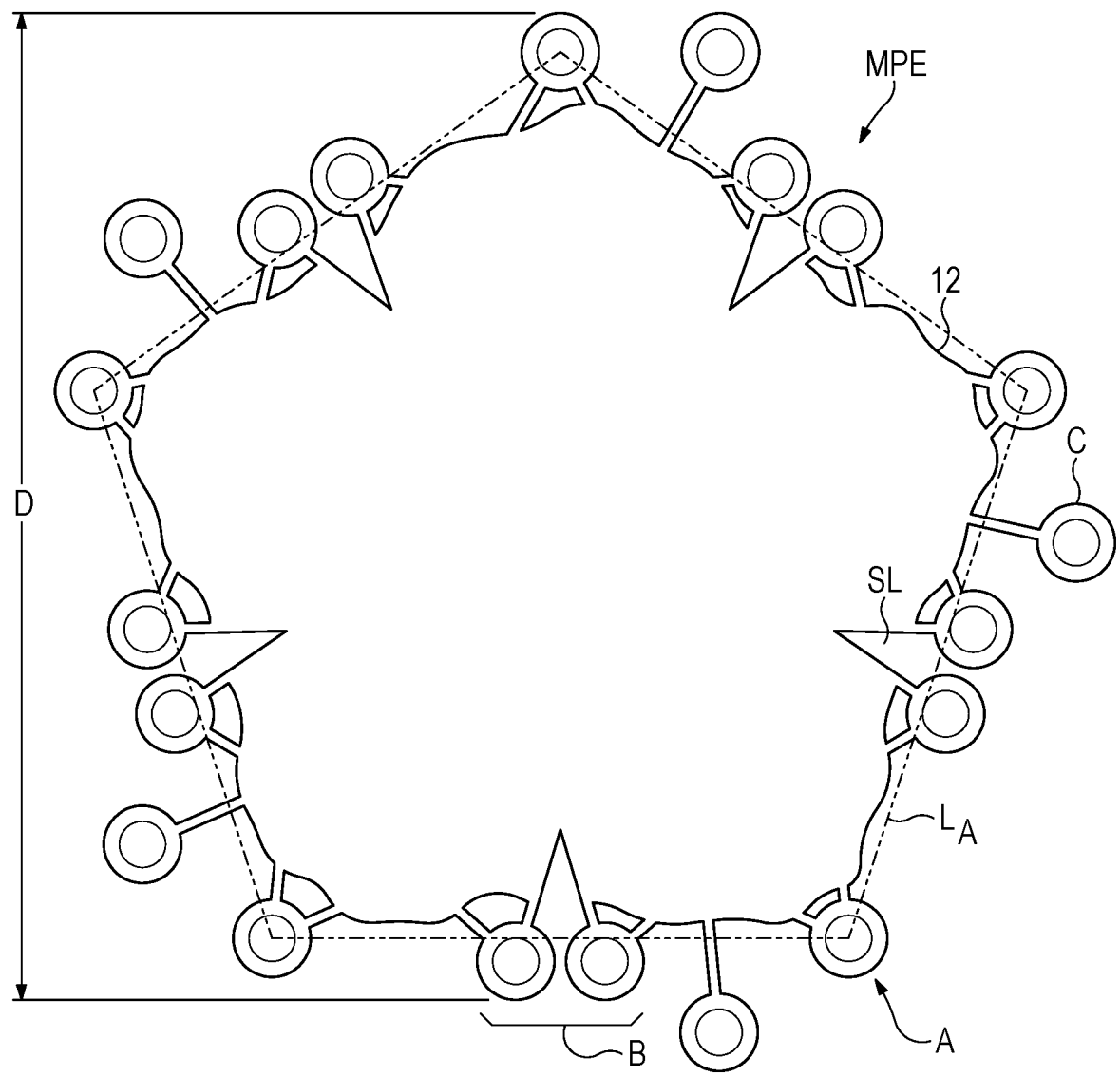
FIG. 3 is a schematic diagram showing a generalized modular element for positioning electrodes on the surface of a head according to the present invention in plan view.

FIG. 3 shows in partial schematic form a preferred modular pentagonal element "MPE" according to the invention, corresponding to one of the pentagonal elements P in FIG. 1. The modular pentagonal element may be formed from a sheet of elastomeric material, such as polyurethane, and is shown in a flat, or planar configuration. The illustration shows a generic body portion 12 of the module, and emphasizes exterior features of the module, particularly five connecting nodes "A," the centers of which lie on a co-planar set of lines "$L_A$" that define a regular pentagon; a corresponding five pairs of warping nodes "B" that lie slightly outside of the lines $L_A$, substantially mid-ay between the nodes A; and five bridging nodes "C" that also lie outside the lines $L_A$, adjacent corresponding instances of the nodes A. Despite these deviations, it is apparent from FIG. 3 that the element P is substantially pentagonal in overall shape.

The connecting nodes A define the pentagonal shape of the modular pentagonal element when the modular element is laid flat, or is in a 2D configuration. The pentagonal shape is particularly advantageous for tessellating a roughly spherical surface like that of a human head. The connecting nodes A are used for connecting one modular element to another.

The purpose of the warping nodes B is to provide for warping a modular element from its ordinary 2D configuration into a 3D domed configuration that can conform to the curvature of the head, by pulling the nodes of each pair of nodes "B" together so that they become congruent with each other. This warping is enabled by the provision of five slits "SL" in the body portion 12 of the modular element, the slits SL corresponding, respectively, to the pairs of nodes B. The slits are void spaces in the sheet material that terminate substantially at a point such as the triangular shaped void spaces indicated.

The purpose of the bridging nodes C will be explained in connection with FIG. 8.

Figure 4:
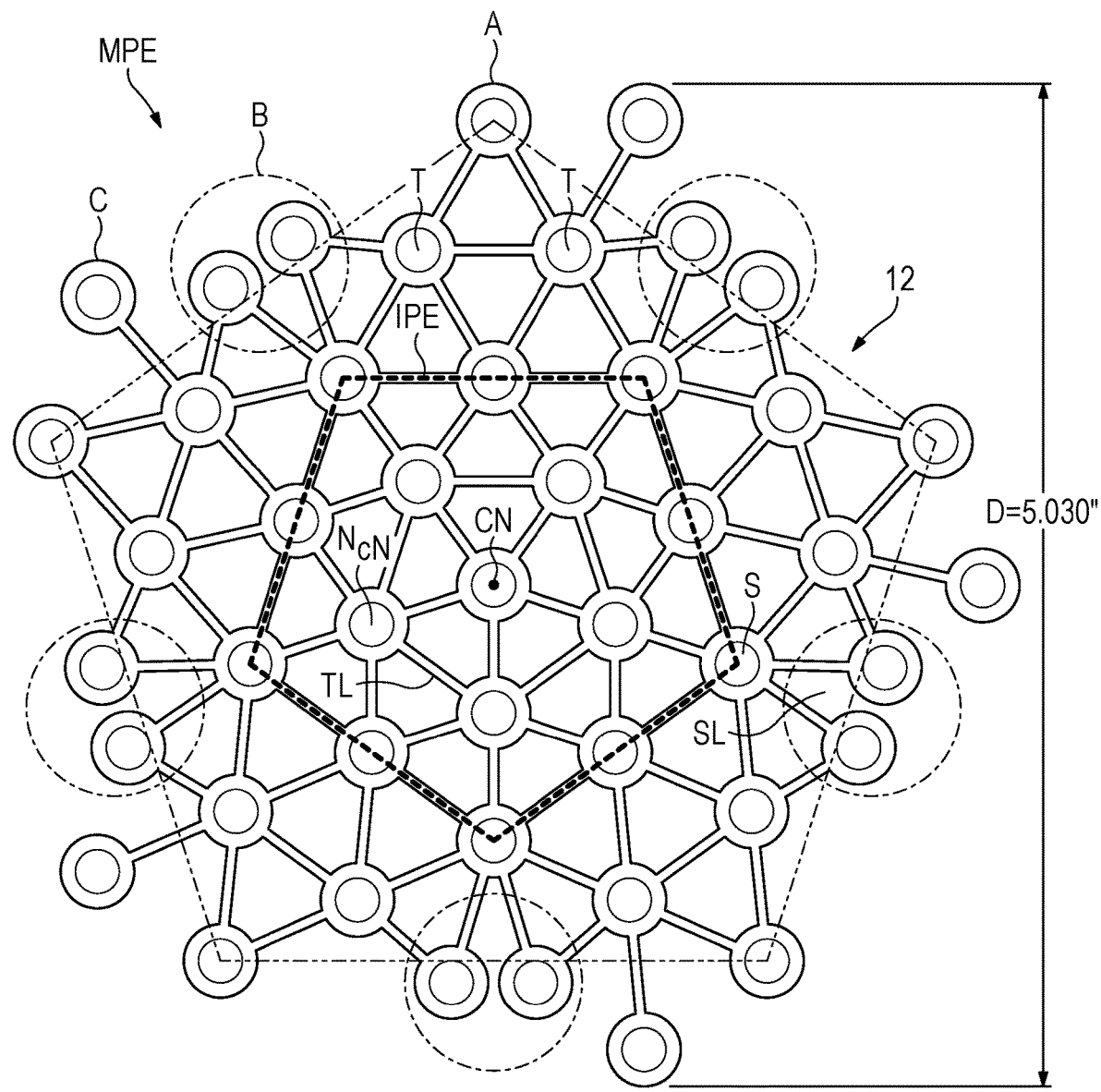
FIG. 4 is a plan view of a preferred modular element for positioning electrodes on the surface of the head according to the invention.

FIG. 4 shows the preferred modular pentagonal element MPE in more detail, showing features of the body portion 12. The drawing is to scale with a preferred overall diametric dimension "D" as indicated. The diametric dimension D may be larger or smaller depending on the size of the head and the number of modular elements employed for covering it.

There is a central node "CN" at the center of the module; which is connected by five tension lines TL to five other nodes "$N_{CN}$" to form a regular pentagonal array; and there are five slit nodes "S" at the vertices of the slits SL. Also as noted previously, there is one bridging node C adjacent each of the nodes A.

Aside from the nodes A, B, C, CN, and S, all the nodes are intra-modularly connected to six nearest neighbor nodes, in hexagonal arrays that become substantially regular when the nodes "B" are pulled together and the module is warped as described above.

The nodes may be provided in the form of holes in the elastomeric sheet, and the tension lines may be defined by larger holes in the elastomeric sheet. This allows for forming the nodes and tension lines together simply by die cutting or etching the sheet to remove the excess material; although this could be done in any other desired manner. Etching has been found to be a particularly cost effective manufacturing method for modular elements according to the present invention, in reduced tooling costs, and it has the advantage of being insensitive to the flexibility of the sheet.

An entire truncated icosahedral neural sensor net, or any number of modular elements therefor, could be formed as just described; and the same could also be formed with an additive manufacturing process such as by use of a 3D printer.

The thickness of the sheet depends on the flexibility or elasticity that is desired for the tension lines, such as between 5 and 15 mils; a preferred example being about 10 mils (i.e., about 0.01").

Where a truncated icosahedral neural sensor net is formed of multiple modules, it is not essential that the modules be identical; although this is generally most desirable from both a cost and utility stand-point.

It is also not essential that the body portions of the modules have the geometry shown in FIG. 4; however, this specific geometry is believed to provide for the advantage of a maximum number of nodes while substantially equalizing the forces on the nodes.

It may also be noted that the spaces between the nodes shown in FIG. 4 could be tessellated further, with additional nodes to increase the node density of the module. For example, additional nodes could be added at the centers of the triangular spaces shown in FIG. 4, connecting to the existing nodes at the vertices thereof. The same is true for the tessellation shown in FIG. 2.

Figure 5:
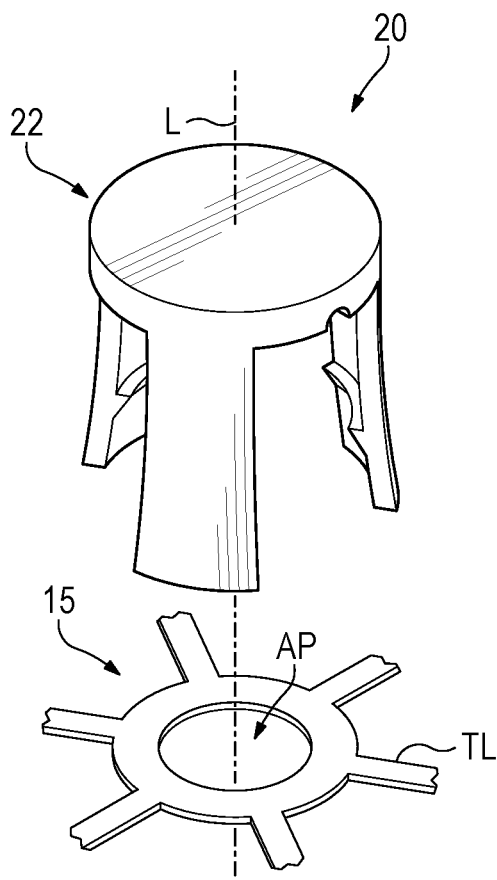
FIG. 5 is an exploded isometric view of an electrode according to the present invention, particularly adapted for use with the modular element of FIG. 2, and a generalized node that is shown broken from the modular element.
Figure 5:
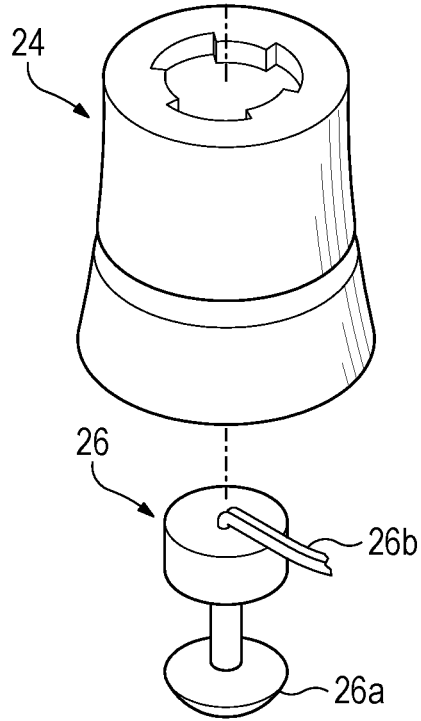
Figure 6:
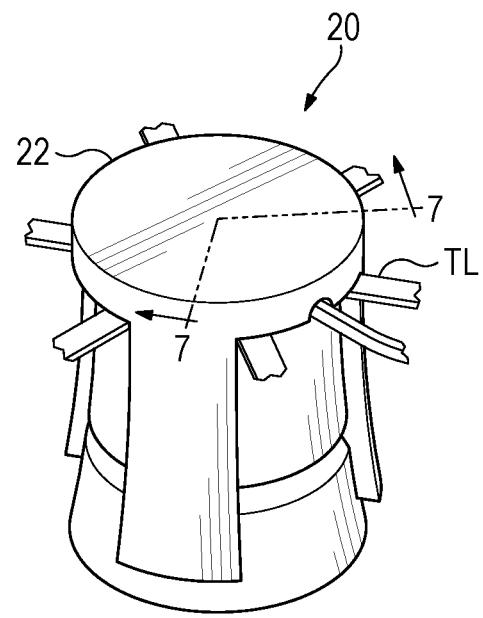
FIG. 6 is an isometric view of the electrode and node of FIG. 5 assembled together.
Figure 7:
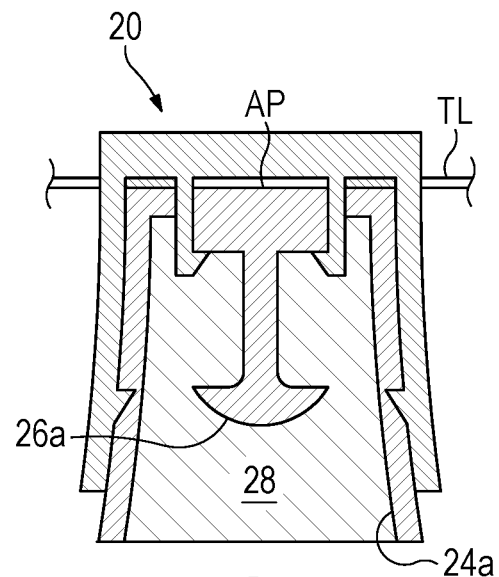
FIG. 7 is a section view of the assembly of FIG. 6, taken along a line 7-7 thereof.

As noted previously, each node is adapted for receiving a respective one of the electrodes. FIGS. 5-7 show an exemplary electrode assembly 20 for use with the modular element 10, and a preferred manner of attaching the electrode assembly to a generalized node 15 of the module. It will be understood that the node 15 could be a stack of nodes that are shared between two or . . . more modules (e.g., the nodes B shown in FIG. 9). The node 15 has an aperture "AP" and, in accord with the preferred embodiment 10, six tension lines "TL" connecting the node 15 to neighboring nodes.

FIG. 5 shows the assembly 20 exploded along an axis "L" that is centered on the aperture AP of the node 15. The assembly 20 includes a capping portion 22, a housing portion 24, and an electrode 26. FIG. 6 shows how the housing portion 24 may be snapped onto the capping portion 22, and FIG. 7 shows how the electrode 26 may be snapped into the housing portion 24. FIG. 5 also shows an absorbent element 28 that may be provided, which may be formed of a foam material, and which can be captured by a foot portion 26a of the electrode 26 as shown, but which could also be captured by the interior surface 24a (see FIG. 7) of the housing 24, such as by the provision of spikes or ridges on that surface.

The absorbent element is for absorbing and thereby retaining an electrically conductive solution or gel that reduces the impedance of the electrical contact between the electrode and the scalp during use of the module 10. An electrical input to, or output from, the electrode 26 may be carried by a single wire conductor 26b as is typical in the art.

Returning to FIG. 4, the preferred modular element MPE has twenty-six interior or "body" nodes that are not shared with other modules. The five nodes A, the five pairs of nodes B, and the five nodes C, may each be shared with five other modules, in which case these groups of nodes may be counted as contributing three additional nodes to the twenty-six body nodes of the module, for a total of twenty-nine nodes per MPE. It is desired to provide for at least 256 electrodes, and this can be accomplished by connecting together nine of the modules MPE.

Figure 8:
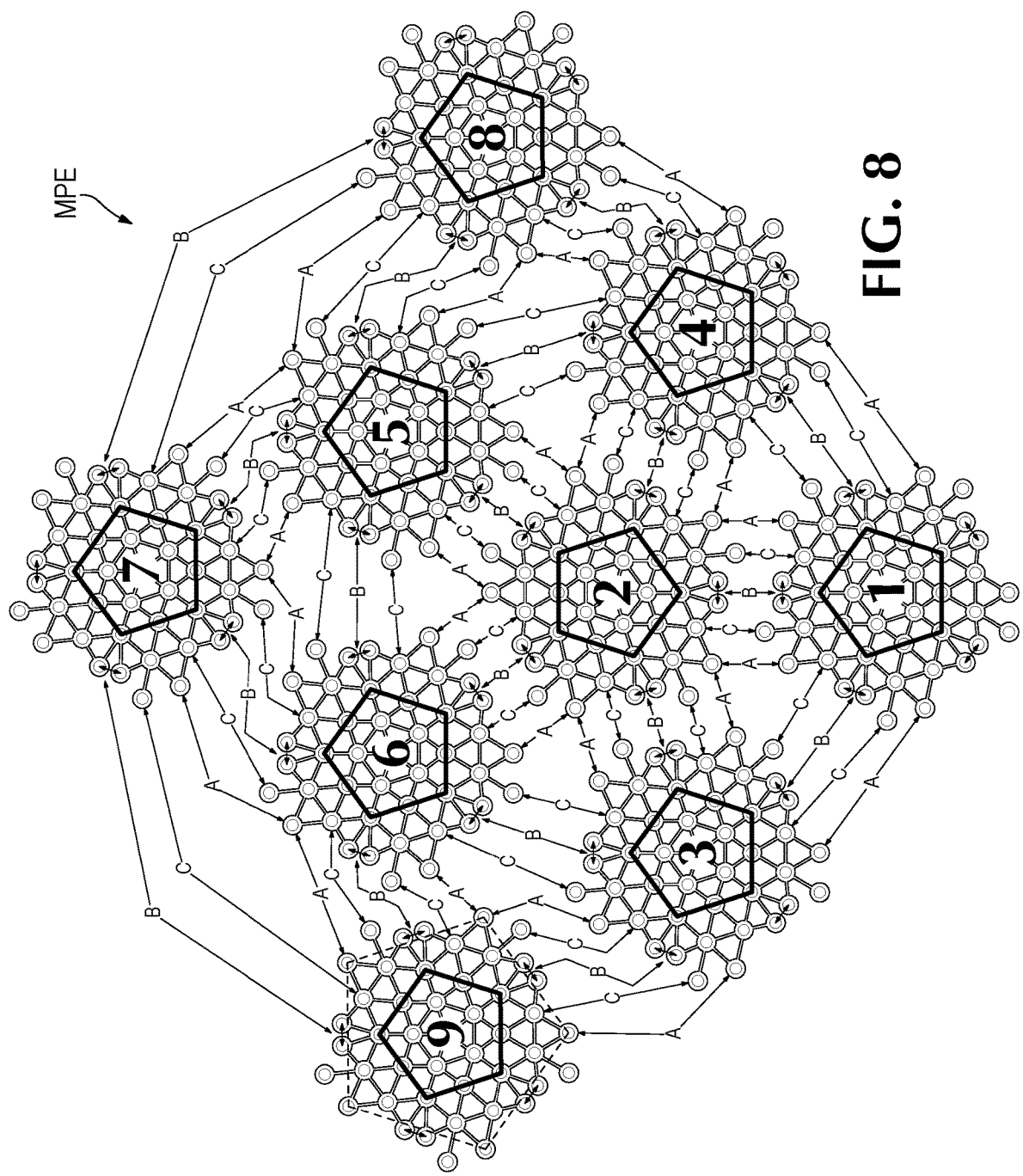
FIG. 8 is a plan view showing nine of the modular elements of FIG. 2 and illustrating interconnections therebetween.

FIG. 8 shows nine of the modules MPE as depicted in FIG. 4, numbered 1-9. The modules numbered 1, 2, 4, 5, 7, and 8 correspond to those shown in FIG. 1.

FIG. 8 also shows the interconnections between all three node types A, B, and C. Any two or more nodes may be joined by manipulating the nodes so that they overlap one another and connecting them together with an electrode assembly.

Figure 9:
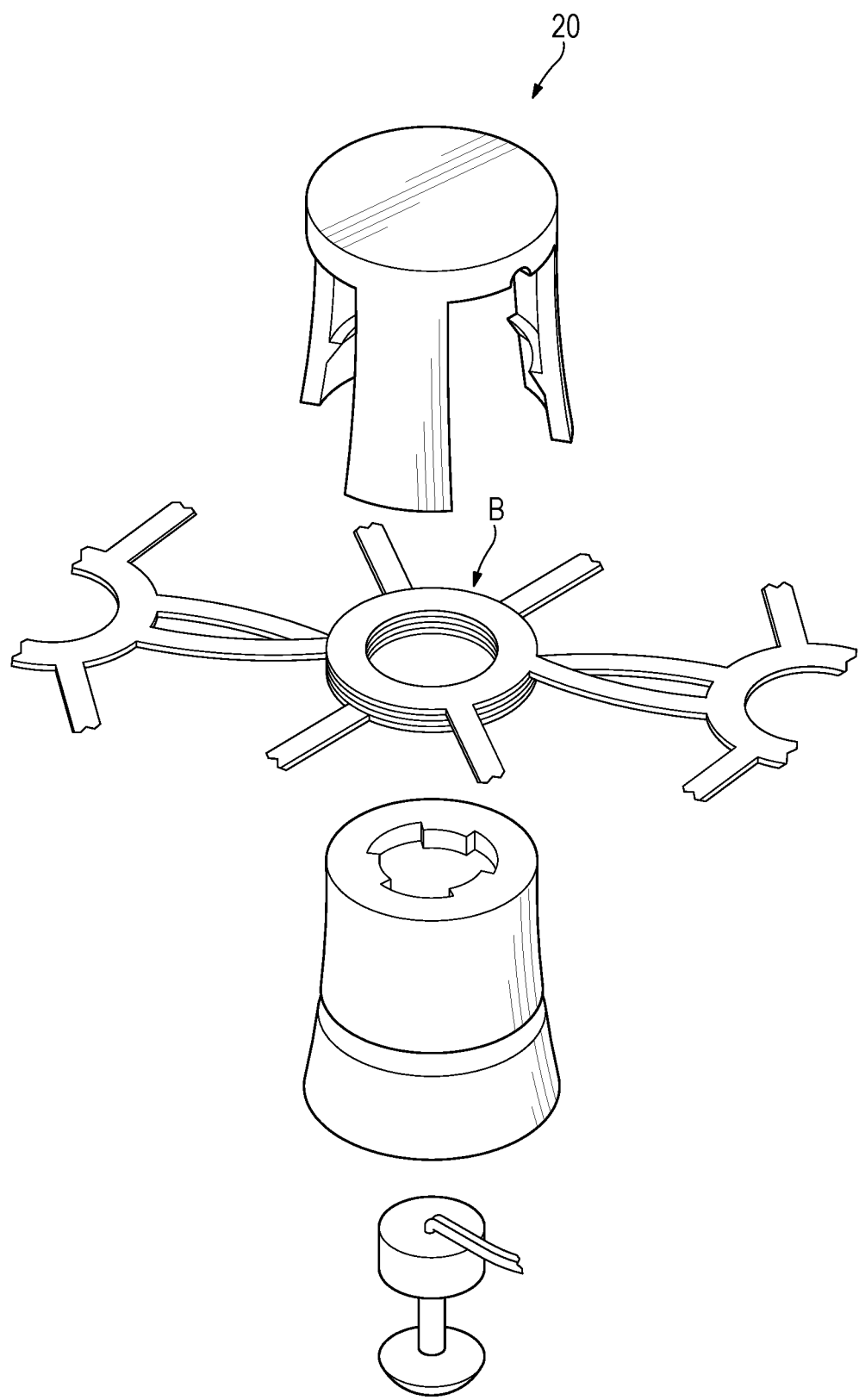
FIG. 9 is an exploded isometric view of the electrode of FIG. 5, with the generalized node replaced with two pairs of nodes B.

FIG. 9 shows the result of such manipulation for two pairs of the nodes B, and how the electrode 20 may be used to maintain the overlapping configuration of the nodes.

As noted previously, joining corresponding A nodes of two modular elements connects one modular element to another; and joining corresponding pairs of B nodes warps the modular elements out of their plan 2D configuration into a domed 3D configuration. It can be appreciated now from FIG. 8 that joining the corresponding bridging nodes C nodes fills in gaps between the modular elements that would not otherwise be bridged by a tension line. The C nodes thereby provide for a desirable feature, though it is not essential, to maintain everywhere throughout a neural sensor net that is formed of multiple modular elements a substantially equalized, radially distributed tension on the nodes.

Finally it may be noted by inspection of FIGS. 8 and 4 that each of the preferred modular pentagonal elements MPE has an inner pentagonal element "IPE" surrounded by outer hexagonally tessellating structure. For additional reference in this regard, compare the modular element MPE shown in FIG. 4 to the modular element MPE associated with the inner pentagonal element numbered 9 in FIG. 8.

In FIG. 8, it is these inner pentagonal elements IPE that are numbered, and they correspond to the pentagonal elements P in FIG. 1. The outer hexagonally tessellating structure of the modular pentagonal elements MPE fills in the space between the inner pentagonal elements to create the hexagonal elements H shown in FIG. 1 when the modular elements are joined together. For example, the three pentagonal elements 4, 5, and 8 and the intervening hexagonal element "H," shown in FIG. 1 may all be formed by joining the three modular pentagonal elements MPE associated with the inner pentagonal elements numbered 4, 5, and 8 in FIG. 8.

Truncated iscosahedral neural sensor nets according to the present invention are a better fit to various head shapes than the original icosahedral GSN, including the ellipsoidal shape (with smaller frontal than parietal regions) that is typical of Caucasians and the more cubical or spherical head shape of many Asians.

Modular elements according to the present invention provide for decreased manufacturing costs by facilitating mass production. Modular elements are preferably used to form truncated icosahedral neural sensor nets, but modular elements according to the invention could also be used to form idosahedral sensor nets like the GSN, as well as other net geometries or configurations.

It is to be understood that, while a specific truncated icosahedral neural sensor net and modular elements therefor has been shown and described as preferred, other configurations could be utilized, in addition to those already mentioned, without departing from the principles of the invention.

The terms and expressions which have been employed in the foregoing specification are used therein as terms of description and not of limitation, and there is no intention in the use of such terms and expressions to exclude equivalents of the features shown and described or portions thereof, it being recognized that the scope of the invention is defined and limited only by the claims which follow.

The invention claimed is:

1. A neural sensor net comprising a plurality of substantially regular pentagonal shaped elements connected to each other with elongate elastic tension lines at their respective vertices, wherein three tension lines form, in combination with three respective sides of three substantially regular pentagonally shaped elements, a substantially regular hexagonal shaped element.

2. A modular element for a neural sensor net for wearing on a head surface, comprising a body formed of a sheet material that defines a plurality of nodes and a plurality of tension lines, wherein the tension lines are elongate segments of the material that join the nodes so as to define legs of triangles of which the nodes define vertices, wherein there are more than fifteen nodes and wherein, with the modular element laid flat, five of the more than fifteen nodes are connecting nodes that define the vertices of a substantially regular pentagon, for connecting the modular element to one or more other modular elements, and ten of the more than fifteen nodes are closely spaced pairs of warping nodes disposed substantially mid-way between the vertices, wherein the nodes of each pair of warping nodes are separated by respective slits in the body of the modular element, the warping nodes and slits for warping the element into a 3D domed configuration for fitting to the head surface.

3. The modular element of claim 2, further comprising at least one additional node that is a bridging node, adjacent and corresponding to one of the connecting nodes, to provide for sharing at least one of the tension lines between the modular element and one other modular element.

4. The modular element of claim 3, wherein there are five of the bridging nodes.

5. The modular element of claim 4, wherein the nodes are annular.

6. The modular element of claim 3, wherein the nodes are annular.

7. The modular element of claim 2, wherein the nodes are annular.

8. A modular element for a neural sensor net for wearing on a head surface, comprising a body formed of a sheet material that defines a plurality of nodes and a plurality of tension lines, wherein the tension lines are elongate segments of the material that join the nodes so as to define legs of triangles of which the nodes define vertices, wherein there are more than fifteen nodes and wherein, with the modular element laid flat, five of the more than fifteen nodes are connecting nodes that define the vertices of a substantially regular pentagon, for connecting the modular element to one or more other modular elements, and ten of the more than fifteen nodes are closely spaced pairs of warping nodes disposed substantially mid-way between the vertices, wherein the nodes of each pair of warping nodes are separated by respective slits in the body of the modular element, the warping nodes and slits for warping the element into a 3D domed configuration for fitting to the head surface, and wherein the modular element is surrounded by an outer substantially regular hexagonal tessellating structure.

9. The modular element of claim 8, in combination with two other substantially identical modular elements, joined together so that the outer substantially regular hexagonal tessellating structure of the three modular elements defines a substantially regular hexagonal shaped element between the three modular elements.

10. The combination of modular elements of claim 9, wherein at least two of the three modular elements further comprises at least one additional node that is a bridging node, adjacent and corresponding to an associated one of the connecting nodes of the at least two of the three modular elements, to provide for sharing at least one of the tension lines between the at least two of the three modular elements.

11. The combination of modular elements of claim 10, where there are five of the bridging nodes for each of the at least two modular elements.

12. The combination of modular elements of claim 11, wherein all three of the modular elements comprise a bridging node.

13. The combination of modular elements of claim 12, wherein there are five of the bridging nodes for each of the three modular elements.

14. The combination of modular elements of claim 13, wherein the nodes are annular.

15. A neural sensor net comprising a plurality of substantially identical, flat modular elements connected to each other so as to cause the otherwise flat modular elements to be warped into respective 3D domed configurations, and so as to define at least one set of three substantially regular pentagonally shaped elements, wherein the three substantially regular pentagonally shaped elements are spaced apart from each other by a corresponding substantially regular hexagonally shaped element.

16. A process for forming a neural sensor net, comprising forming a plurality of substantially identical, flat modular substantially regular pentagonally shaped elements and connecting the modular elements together so as to cause the otherwise flat modular elements to be warped into respective 3D domed configurations, and so as to define at least one set of three substantially regular pentagonally shaped elements, wherein the three substantially regular pentagonally shaped elements are spaced apart from each other by a corresponding substantially regular hexagonally shaped element.

* * * * *